(12) United States Patent
Huang et al.

(10) Patent No.: US 10,273,064 B2
(45) Date of Patent: Apr. 30, 2019

(54) LID OPENING STRUCTURE AND PHYSIOLOGICAL DETECTING DEVICE

(71) Applicant: TAIDOC TECHNOLOGY CORPORATION, New Taipei (TW)

(72) Inventors: Yi-Hsin Huang, New Taipei (TW); Ying-Chih Liao, New Taipei (TW)

(73) Assignee: TAIDOC TECHNOLOGY CORPORATION, New Taipei (TW)

( * ) Notice: Subject to any disclaimer, the term of this patent is extended or adjusted under 35 U.S.C. 154(b) by 262 days.

(21) Appl. No.: 15/345,099

(22) Filed: Nov. 7, 2016

(65) Prior Publication Data

US 2017/0137186 A1    May 18, 2017

(30) Foreign Application Priority Data

Nov. 16, 2015 (TW) .............................. 104137779 A

(51) Int. Cl.
| | |
|---|---|
| *B65D 39/00* | (2006.01) |
| *B65D 51/24* | (2006.01) |
| *B65D 43/16* | (2006.01) |
| *A61B 5/00* | (2006.01) |
| *A61B 5/145* | (2006.01) |
| *A61B 10/00* | (2006.01) |
| *A61B 5/15* | (2006.01) |

(52) U.S. Cl.
CPC .......... *B65D 51/24* (2013.01); *A61B 5/14532* (2013.01); *A61B 5/43* (2013.01); *B65D 43/162* (2013.01); *B65D 43/164* (2013.01); *A61B 5/150358* (2013.01); *A61B 10/007* (2013.01); *A61B 10/0045* (2013.01); *A61B 10/0096* (2013.01); *A61B 2010/0077* (2013.01); *B65D 2543/00833* (2013.01)

(58) Field of Classification Search
CPC .................................. G01N 1/00; B65D 39/00
See application file for complete search history.

(56) References Cited

U.S. PATENT DOCUMENTS 5,174,462 A * 12/1992 Hames ...................... B65F 7/00
                                                              220/522
9,823,234 B2 * 11/2017 Logel ................. B65D 83/0829

* cited by examiner

*Primary Examiner* — Jyoti Nagpaul
(74) *Attorney, Agent, or Firm* — Chun-Ming Shih

(57) ABSTRACT

A lid opening structure and a physiological detection device are provided. The lid opening structure is adapted for the physiological detection device and for being mounted on a lid body of a container. The lid body includes a flange portion and a pivot portion. The lid opening structure includes a first cover portion disposed on a side corresponding to the flange portion and having an engaging portion for clamping the flange portion, and a second cover portion disposed on a side corresponding to the pivot portion. When applying a force on the first cover portion along a lid opening direction, the physiological detection device is fixed on the lid body by stopping the force applied along the lid opening direction by the second cover portion, and the lid body of the container is opened. The combined use of the container and the physiological detection device increases the convenience of use.

20 Claims, 8 Drawing Sheets

LID OPENING STRUCTURE AND PHYSIOLOGICAL DETECTING DEVICE

BACKGROUND OF THE INVENTION

Field of the Invention

The present invention generally relates to a lid opening structure and a physiological detection device, in particular, to a lid opening structure which can be quickly detached from or mounted on a lid body of a container and a physiological detection device adapted for being mounted on a lid body for use.

Description of the Related Art

With the development of modern technology and changes in lifestyles, some physiological examinations that must be conducted in a hospital in the past are able to be conducted at home now. Changes in lifestyles have resulted in an increased number of chronic disease patients, and this also speeds up the development of the home health care industry. Among a wide range of examinations for physiological parameters that can be conducted at home, blood glucose monitoring is one of the most important physiological examinations for which a diabetic patient needs to measure frequently and to keep a long-term habit of measurements.

When performing a blood glucose measurement, a user needs to take a blood glucose test strip out from a test strip vial first, and insert the test strip into a blood glucose meter. In addition, a lancet and/or a lancing device are prepared for pricking a fingertip to obtain a blood sample. After pricking, an appropriate amount of blood is squeezed out from the fingertip, and applied into the test strip, such that a measurement procedure of the blood glucose meter is activated. From the description above, it could be known that the user needs to prepare many related items in advance for performing a blood glucose measurement. Said items include a blood glucose meter, a lancet, a lancing device, a test strip stored in a test strip vial, etc.

If the item is not properly kept or stored, the user will easily forget where the item has been placed. Particularly, a diabetic patient needs to conduct blood glucose measurements three times a day with meals, or even more tests including measurements before and after meals for better health monitoring. Therefore, a patient is highly dependent on said items for conducting daily physiological data monitoring. It will be extremely troublesome if any one of said items is lost. The physiological data cannot be completely recorded, and the patient's condition may become worse in some serious cases.

A large proportion of patients having chronic diseases are elders. Nowadays, the phenomenon of global population aging has become increasingly apparent. As a high risk group for developing chronic diseases, elders tend to have poor memories. Accordingly, for related manufacturers, how to help users to simplify the preparation process for measurements and to build a user friendly environment are issues waiting to be solved.

SUMMARY OF THE INVENTION

For solving the issues mentioned above, a lid opening structure is provided in the present invention. Through the lid opening structure, a physiological detection device can be mounted on or detached from a container by applying a force along a single direction. By simply providing a direction for applying force, the lid opening structure and the physiological detection device can be combined and used for opening the container.

A physiological detection device is provided in accordance with the present invention. Through the combined use of the physiological detection device and a container at the same time, and through a quick mounting on or detachment from the container, the preparation steps can be simplified and a user friendly environment can be provided. In a measuring process, a user can easily access a detection related material in the container, and a situation in which a detection related item is lost due to separate or improper storage can be prevented.

For achieving above purposes, a lid opening structure is provided for being mounted on a lid body of a container. The lid body comprises a flange portion and a pivot portion, the flange portion is disposed in a side opposite to the pivot portion, and the pivot portion is configured to connect a main body and the lid body of the container. The lid opening structure may comprise: a first cover portion, which is disposed on a side corresponding to the flange portion and has an engaging portion for clamping the flange portion; and a second cover portion, which is disposed on a side corresponding to the pivot portion. When applying a force on the first cover portion along a lid opening direction, the physiological detection device is fixed on the lid body by stopping the force applied along the lid opening direction by the second cover portion, and the lid body of the container is opened.

According to an embodiment of the present invention, the first cover portion further comprises an interference portion, which is disposed on ends of two side edges of the first cover portion and is configured for clamping the lid body and/or the main body.

According to an embodiment of the present invention, the physiological detection device further comprises a guide portion for guiding the physiological detection device to be mounted on the lid body.

According to an embodiment of the present invention, the guide portion is a notch, which is disposed on the ends of two side edges of the first cover portion to provide a space for deformation of the interference portion when the physiological detection device being mounted on or detached from the lid body.

According to an embodiment of the present invention, a length of the first cover portion is longer than half of a perimeter of the lid body matched with the first cover portion.

According to an embodiment of the present invention, the second cover portion is disposed in a position corresponding to a peripheral portion of the lid body which does not covered by the first cover portion.

According to an embodiment of the present invention, the second cover portion further comprises a stop pillar, which is disposed on an inner side surface of the second cover portion, and is extended outward from the inner side surface of the second cover portion.

According to an embodiment of the present invention, there is a plurality of stop pillars symmetrically distributed on two parts of the inner side surface of the second cover portion.

According to an embodiment of the present invention, each of the first cover portion and the second cover portion is a thin wall with a uniform thickness, the interference portion is a thickened portion of the thin wall, the engaging portion is an aperture, and a length of the engaging portion is corresponding to a length of the flange portion.

According to an embodiment of the present invention, the container is configured for storing a disposable material used together with the physiological detection device.

Viewed from another aspect, a physiological detection device is provided in according to the present invention. The physiological detection device is adapted for being mounted on a container, wherein the container comprises a lid body and a main body, the lid body comprises a flange portion and a pivot portion, the flange portion is disposed in a side opposite to the pivot portion, and the pivot portion is configured to connect a main body and the lid body of the container. The physiological detection device comprises a first cover portion disposed on a side corresponding to the flange portion, and the first cover portion comprises: an engaging portion, which is disposed on a position of the first cover portion corresponding to the flange portion and is configured for clamping the flange portion; and an interference portion, which is disposed on two side edges of the first cover portion and is configured for clamping the lid body and/or the main body. When assembling the first cover portion on the flange portion, a force is applied on the physiological detection device along a direction toward the pivot portion, such that the physiological detection device is mounted on the lid body.

According to an embodiment of the present invention, the physiological detection device may further comprise a guide portion for guiding the physiological detection device to be mounted on the lid body.

According to an embodiment of the present invention, the guide portion is a notch, which is disposed on ends of two side edges of the first cover portion to provide a space for deformation of the interference portion when the physiological detection device being mounted on or detached from the lid body.

According to an embodiment of the present invention, a length of the first cover portion is longer than half of a perimeter of the lid body.

According to an embodiment of the present invention, the physiological detection device further comprises a second cover portion, which is disposed on a side corresponding to the pivot portion; wherein when applying a force on the first cover portion along a lid opening direction, the physiological detection device is fixed on the lid body by stopping the force applied along the lid opening direction by the second cover portion, and the lid body of the container is opened.

According to an embodiment of the present invention, the second cover portion is disposed in a position corresponding to a peripheral portion of the lid body which does not covered by the first cover portion.

According to an embodiment of the present invention, each of the first cover portion and the second cover portion is a thin wall with a uniform thickness, the interference portion is a thickened portion of the thin wall, the engaging portion is an aperture, and a length of the engaging portion is corresponding to a length of the flange portion.

According to an embodiment of the present invention, the second cover portion further comprises a stop pillar, which is disposed on an inner side surface of the second cover portion, and is extended outward from the inner side surface of the second cover portion.

According to an embodiment of the present invention, there is a plurality of stop pillars symmetrically distributed on two parts of the inner side surface of the second cover portion.

According to an embodiment of the present invention, the physiological detection device further comprises an opening for accommodating a disposable material used together with the physiological detection device.

According to an embodiment of the present invention, the physiological detection device is a blood glucose meter, and the container is a test strip vial.

According to an embodiment of the present invention, the physiological detection device further comprises: a micro processing unit for performing a detection of a physiological parameter; and a display unit coupled to the micro processing unit, which is configured to display a related information of the physiological detection device.

According to an embodiment of the present invention, the physiological detection device further comprises: a power unit disposed on a bottom portion of the physiological detection device for serving as a power source of the physiological detection device; and an operating unit coupled to the micro processing unit for operating the physiological detection device.

Based on above, a lid opening structure and a physiological detection device provided in the present invention allow a physiological detection device to be mounted on or detached from a lid body of a container by applying a force along a single direction, such that a user can access the physiological detection device and a necessary item which is related to the physiological detection and stored in the container at the same time in the preparation of measurement. When opening the lid body of the container, the physiological detection device is able to be fixed on the lid body of the container. The user is able to combine the physiological detection device and the container and to operate through simple steps, thereby preventing a troublesome situation in which items related to measurement are accidentally lost somewhere and a measurement cannot be conducted smoothly.

In order to make the aforementioned features and advantages of the present invention more comprehensible, the following embodiments accompanied with figures are described in detail below.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF THE PREFERRED EMBODIMENTS

The phenomenon of global population aging has become increasingly apparent, and long-term health monitoring for chronic disease patients has become an important issue. Take a diabetic patient for example, a user needs to prepare a lancet, a lancing device, a blood glucose meter, and a test vial which stores blood glucose test strips before conducting a blood glucose measurement. The items for measurement are various and can be easily lost. Particularly, a diabetic patient needs to conduct blood glucose measurements three times a day with meals and has a high frequency of daily measurements. If any one of said items for measurement is lost, it will be very troublesome for the patient, and will be disadvantaged in the completeness of continuous data records.

In contrast, embodiments of the present invention allow a physiological detection device to be mounted on or detached from a lid body of a container by applying a force along a single direction, such that a user can easily access a physiological detection device and a measurement related item stored in a container at the same time, and those measurement related items/accessories will not easily lost. When opening a lid body, a physiological detection device can still be fixed on the lid body by utilizing a lid opening structure, thereby providing a friendly environment for a user to easily conduct a physiological data measurement. Embodiments of the present invention will be described in further details below in reference to the accompanying figures. The accompanying figures illustrate exemplary embodiments of the present invention, in which the same reference sign indicates the same or a similar element.

Figure 1A:
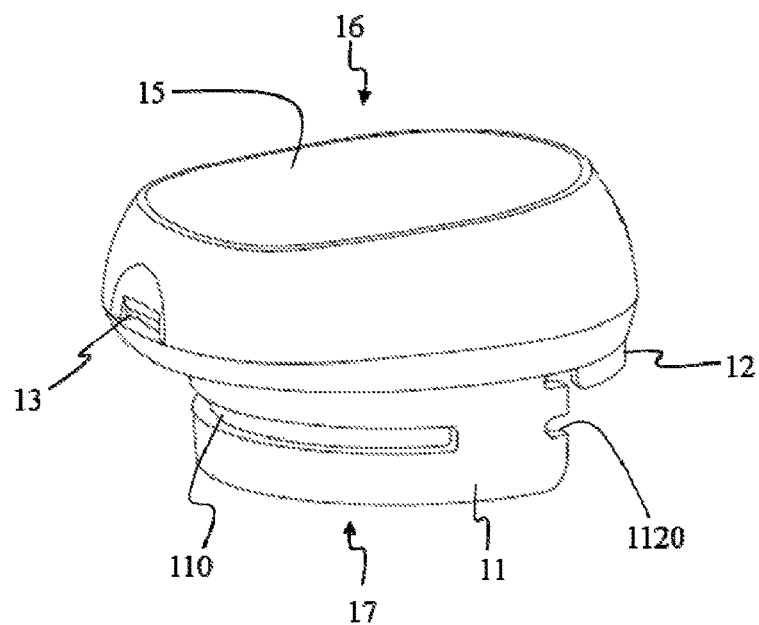
FIG. 1A shows a schematic perspective view of a first preferred embodiment of a physiological detection device according to the present invention.
Figure 1B:
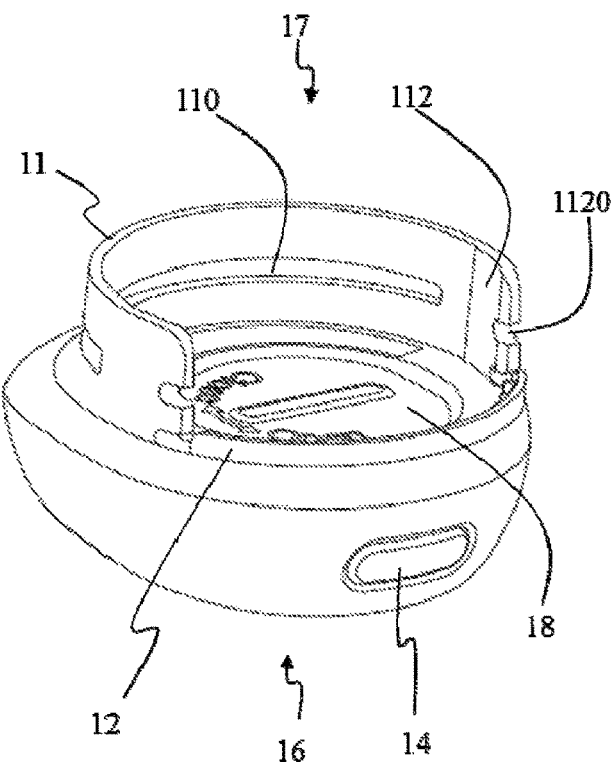
FIG. 1B shows the physiological detection device in FIG. 1A from another angle of view.
Figure 1C:
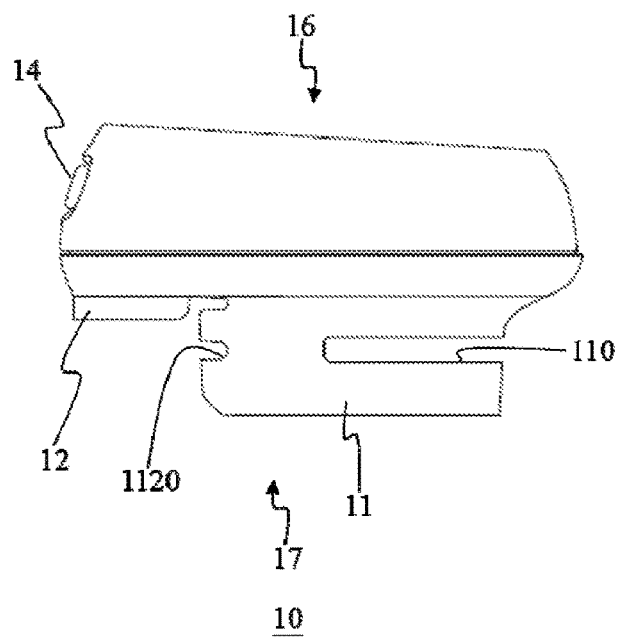
FIG. 1C shows a side view of a first preferred embodiment of a physiological detection device according to the present invention.
Figure 1D:
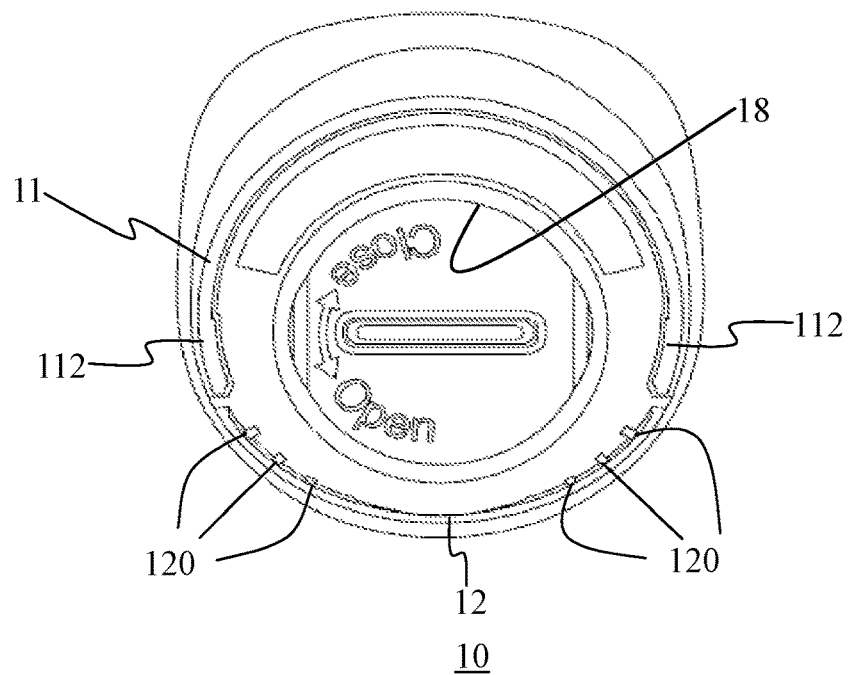
FIG. 1D shows a bottom view of a first preferred embodiment of a physiological detection device according to the present invention.

FIG. 1A shows a schematic perspective view of a first preferred embodiment of a physiological detection device according to the present invention. FIG. 1B shows the device in FIG. 1A from another angle of view. FIG. 1C shows a side view of the first preferred embodiment of a physiological detection device according to the present invention. FIG. 1D shows a bottom view of the first preferred embodiment of a physiological detection device according to the present invention. Please refer to FIG. 1A to FIG. 1D, in the embodiment, a physiological detection device (10) is provided for measuring at least one physiological parameter. Preferably, the physiological parameter can be obtained by performing a directly measurement on an animal, for example, measuring heartbeat, blood oxygen level, the number of steps walked and so on. The physiological parameter can also be obtained by performing a measurement on a sample from an animal in vitro. The sample can include but not limited to blood, urine, serum, cerebrospinal fluid, spinal fluid or other body fluids. More preferably, the physiological parameter can be levels of blood glucose, blood cell, glycated hemoglobin (HbA1c), cholesterol, uric acid, urinary protein, hormone, or other targets for detecting liver function. However, the present invention is not limited thereto.

The physiological detection device (10) has a top portion (16) and a bottom portion (17). Preferably, the top portion (16) includes an opening (13), a micro processing unit, an operating unit (14) and a display unit (15). Each of these structures will be described in more details below. A lid opening structure is disposed on the bottom portion (17). Preferably, the lid opening structure and the physiological detection device (10) are integrally formed. The lid opening structure includes a first cover portion (11) and a second cover portion (12). Preferably, each of the first cover portion (11) and the second cover portion (12) is a thin wall with a uniform thickness. More preferably, the thin wall consists of a plastic material; however, the present invention is not limited thereto. For example, the thin wall can also be made of an elastic material. A person skilled in the art can change the material of the thin wall if needed.

Figure 2A:
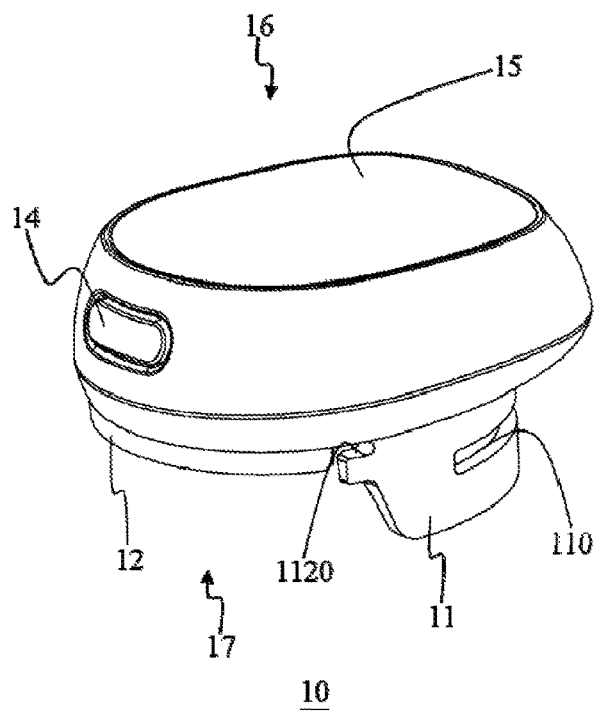
FIG. 2A shows a schematic perspective view of a second preferred embodiment of a physiological detection device according to the present invention.
Figure 2B:
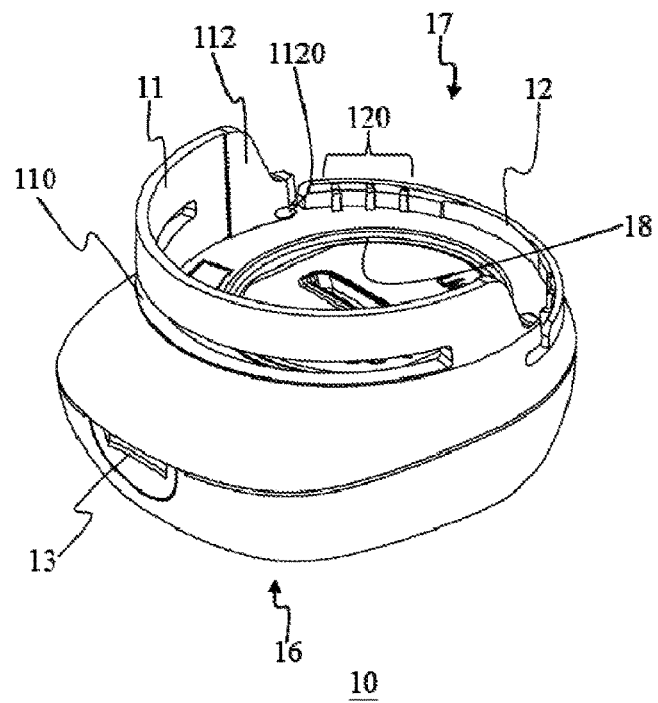
FIG. 2B shows the physiological detection device in FIG. 2A from another angle of view.
Figure 2C:
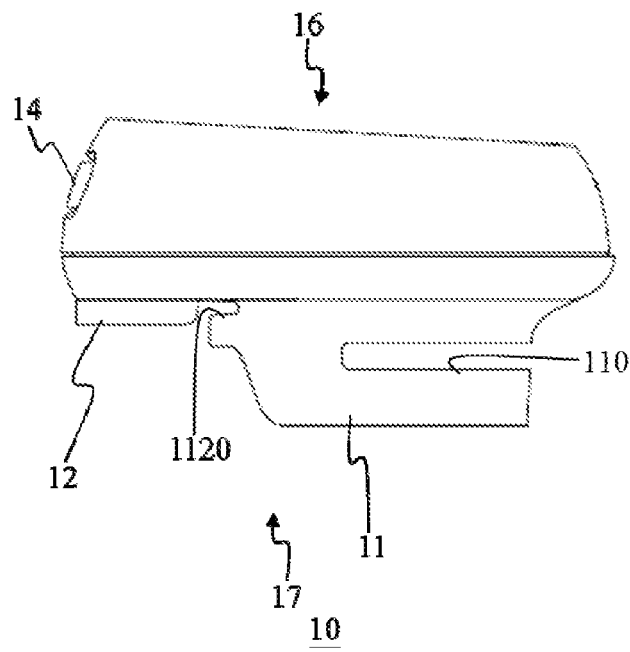
FIG. 2C shows a side view of a second preferred embodiment of a physiological detection device according to the present invention.
Figure 2D:
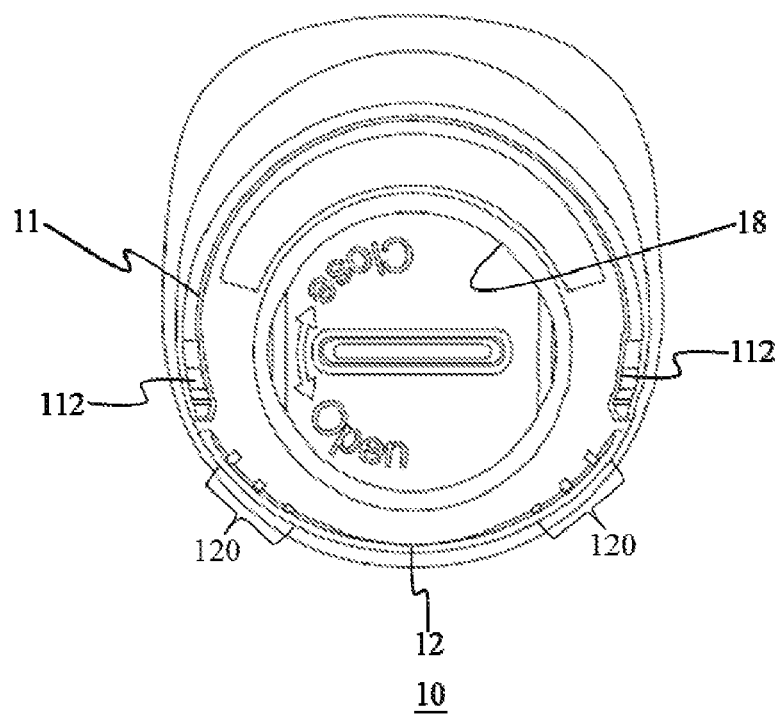
FIG. 2D shows a bottom view of a second preferred embodiment of a physiological detection device according to the present invention.
Figure 3:
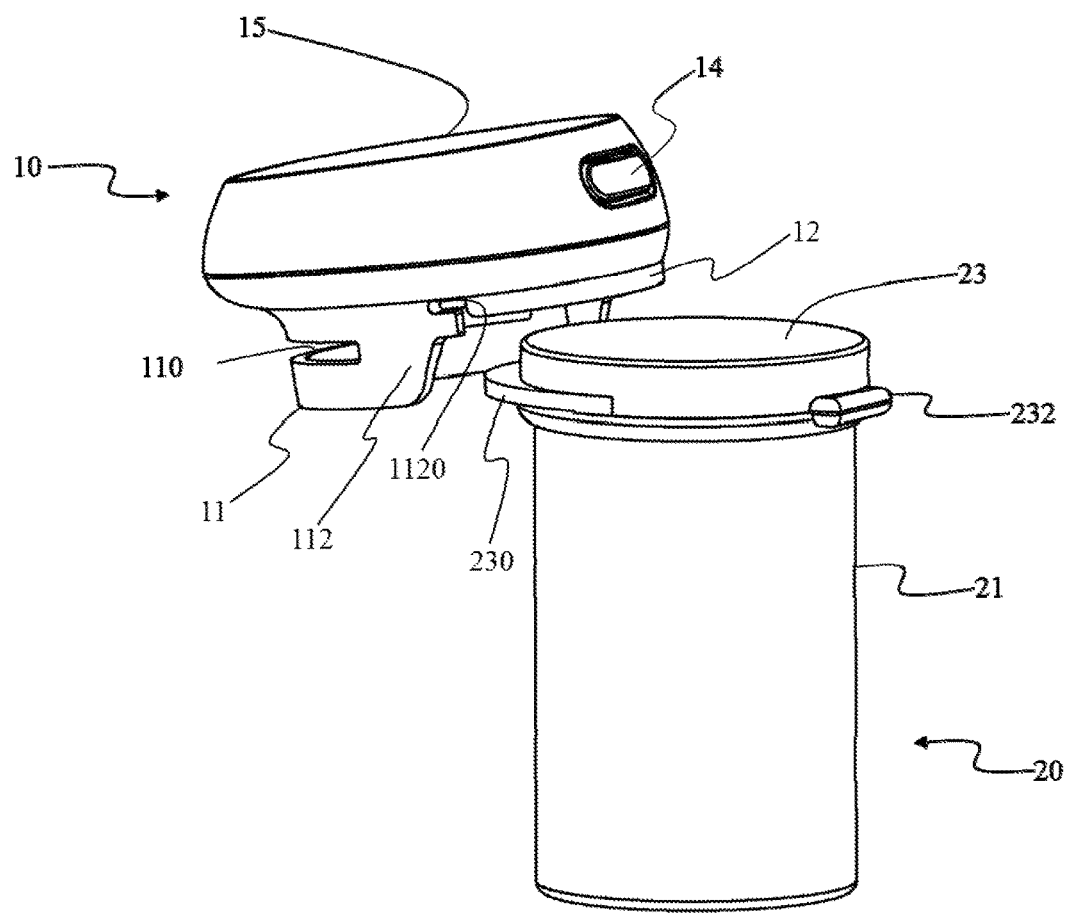
FIG. 3 shows a schematic view illustrating a physiological detection device of a second preferred embodiment according to the present invention, which is prepared to be mounted on a container.
Figure 6:
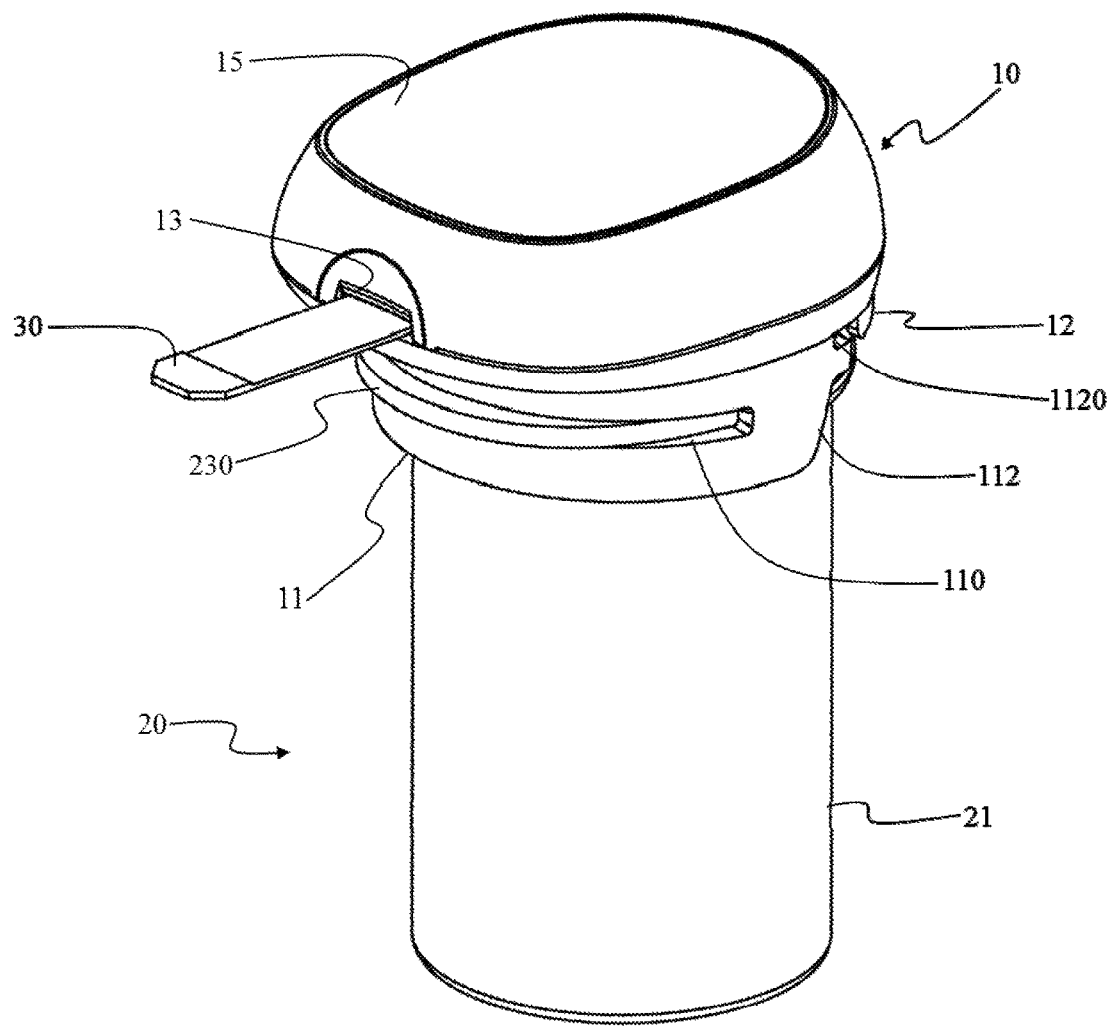
FIG. 6 shows a schematic view illustrating a physiological detection device of a second preferred embodiment according to the present invention, which is mounted on a container and is in a use state.

FIG. 3 shows a schematic view illustrating a physiological detection device of a second preferred embodiment according to the present invention, which is prepared to be mounted on a container. Please refer to FIG. 2A to FIG. 3. In the embodiment, the lid opening structure is configured for being mounted on a lid body of a container (20). The container (20) includes a main body (21) and a lid body (23). Preferably, the container (20) is a sealed container formed by assembling the main body (21) and the lid body (23), and can be opened. The main body (21) is configured for storing a disposable material (30) (as shown in FIG. 6) used together with the physiological detection device (10). Preferably, a drying agent is provided inside the main body (21) for preventing the disposable material from wet damage, which may affect the effectiveness of detection. More preferably, the drying agent is provided on an inner sidewall surface of the main body (21). For example, the physiological detection device (10) is a blood glucose meter, and the disposable material (30) is a blood glucose test strip. Preferably, the container (20) is a test strip vial. However, the present invention is not limited thereto. To be specifically, the lid opening structure is detachably disposed on the lid body (23) of the container (20). Preferably, the shape of the lid body (23) can be circular or elliptical, but the present invention is not limited thereto. The lid body (23) includes a flange portion (230) and a pivot portion (232), and the flange portion (230) is disposed in a side opposite to the pivot portion (232). Preferably, the flange portion (230) is tongue-shaped. More specifically, a user can use the flange portion (230) as a point of application to open the lid body (23). The pivot portion (232) is configured to connect the main body (21) and the lid body (23) of the container (20). Preferably, the main body (21) and the lid body (23) cannot be completely detached from each other. More preferably, the main body (21), the lid body (23) and the pivot portion (232) are integrally formed. However, the present invention is not limited thereto.

FIG. 2A shows a schematic perspective view of a second preferred embodiment of a physiological detection device according to the present invention. FIG. 2B shows the device in FIG. 2A from another angle of view. FIG. 2C shows a side view of the second preferred embodiment of a physiological detection device according to the present invention. FIG. 2D shows a bottom view of the second preferred embodiment of a physiological detection device according to the present invention. Please refer to FIG. 2A to FIG. 2D and FIG. 3. In the embodiment, the first cover portion (11) is disposed on a side corresponding to the flange portion (230). Preferably, the first cover portion (11) includes an engaging portion (110) and an interference portion (112), and the engaging portion (110) is configured for clamping the flange portion (230). Preferably, the engaging portion (110) is disposed in a central region of the first cover portion (11). More preferably, the engaging portion (110) is an aperture. More specifically, a length range of the engaging portion (110) is corresponding to a length range of the flange portion (230).

The interference portion (112) is disposed on ends of two side edges of the first cover portion (11) for clamping the main body (21) and/or the lid body (23). More specifically, the interference portion (112) is disposed in an inner side of the first cover portion (11). Preferably, the interference portion (112) is a thickened portion of the thin wall of the first cover portion (11), and has a bilateral symmetrical shape. Please refer to FIG. 1B and FIG. 2B, it is worth to be mentioned that the physiological detection devices (10) according to the first and second preferred embodiments of the present invention are similar but different in the shape and size of area. In the first preferred embodiment, the area of the interference portion (112) is larger. There is a larger contact interference between the interference portion (112) and the lid body (23) and/or the main body (21) when the physiological detection device being mounted on or detached from the lid body; therefore, a user needs to apply a larger force. Correspondingly, the assembled structure is much more stable. In the second preferred embodiment, the area of the interference portion (112) is smaller. There is a smaller contact interference between the interference portion (112) and the lid body (23) and/or the main body (21) when the physiological detection device being mounted on or detached from the lid body; therefore, the force applied by a user could be smaller. Correspondingly, it's easier to disassemble the structure. If needed, a person skilled in the art can change the shape and size of area of the interference portion.

Preferably, the physiological detection device (10) further includes a guide portion (1120) for guiding the physiological detection device (10) to be prepared for being mounted on the lid body. Preferably, the guide portion (1120) is a notch, which is disposed on the ends of two side edges of the first cover portion. More preferably, an opening of the notch is parallel to the lid body. More specifically, the guide portion (1120) is capable of identifying and indicating a position for mounting, and this helps a user to align the guide portion (1120) of the physiological detection device (10) with an edge of the flange portion (230) of the lid body (23), such that an orientation for mounting the physiological detection device (10) can be determined. It is worth mentioned that the guide portion (1120) is further configured for providing a space for the deformation of the interference portion (112), which is generated when the physiological detection device (10) being mounted on or detached from the lid body (23). Preferably, the guide portion (1120) is not limited to a single notch structure, and there can be a plurality of notches arranged in a top-bottom arrangement (as shown in FIG. 1C).

Figure 4:
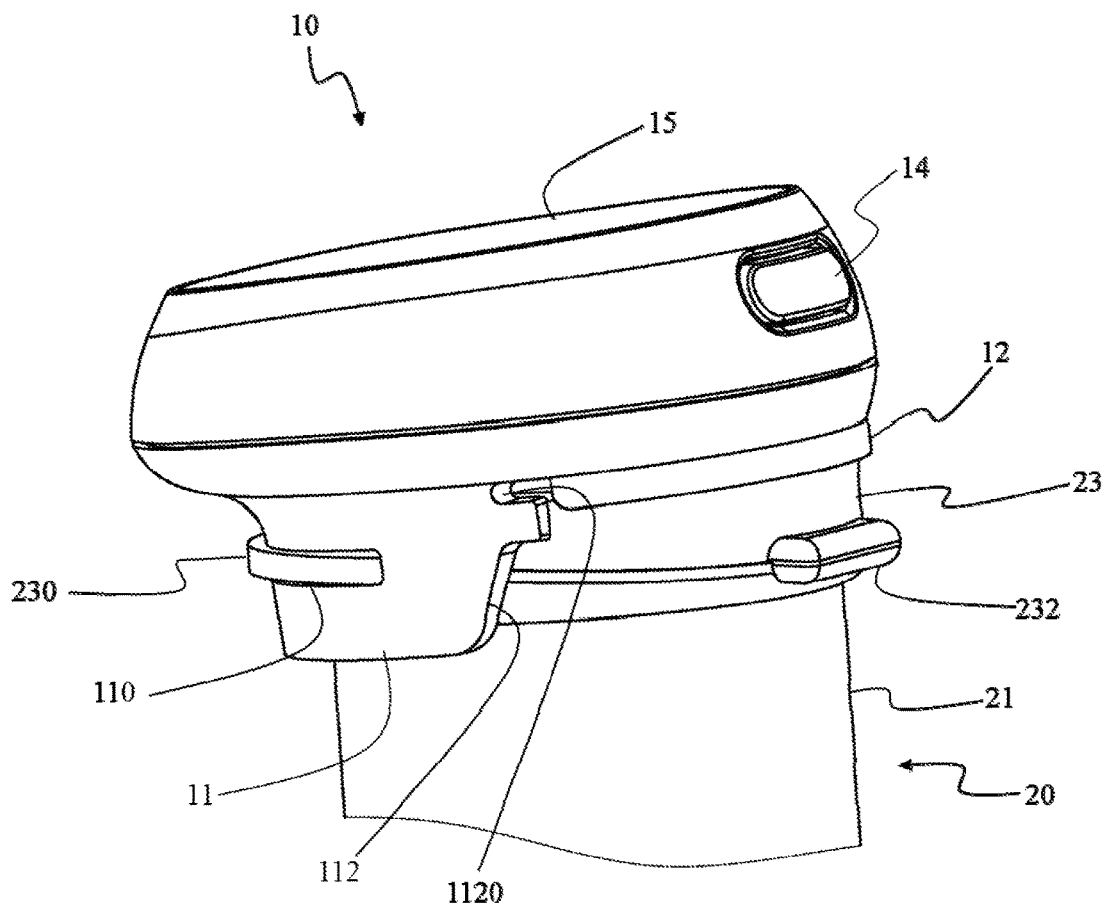
FIG. 4 shows a schematic view illustrating a physiological detection device of a second preferred embodiment according to the present invention, which is mounted on a lid body of a container.

FIG. 4 shows a schematic view illustrating a physiological detection device of a second preferred embodiment according to the present invention, which is mounted to a lid body of a container. Please refer to FIG. 4. In the embodiment, the second cover portion (12) is disposed on a side corresponding to the pivot portion (232). Preferably, the second cover portion (12) is a retaining wall structure. More preferably, a height of the second cover portion (12) is less than a height of the lid body (23). It is worth mentioned that the first cover portion (11) and the second cover portion (12) are arranged in a region defined by the circumference of the lid body (23), and the shape of the lid body (23) is, for example, a circle. Preferably, a length of the first cover portion (11) is longer than half of a perimeter of the lid body (23) matched with the first cover portion (11). The second cover portion (12) is disposed in a position corresponding to a peripheral portion of the lid body (23) which does not covered by the first cover portion (11). More specifically, when the length of the first cover portion (11) is longer than half of a perimeter of the lid body (23), the interference portion (112) disposed on the ends of two side edges of the first cover portion (11) would contract inward along a corresponding arc angle, thereby generating an inward force toward the center of circle, such that the fixation of the physiological detection device (10) on the lid body (23) can be strengthened. However, the present invention is not limited thereto.

Please refer to FIG. 1D, FIG. 2B and FIG. 2D. In the embodiment, the second cover portion (12) further includes a stop pillar (120). The stop pillar (120) is disposed on an inner side of the second cover portion (12), and is extended outward from the inner side surface of the second cover portion (12). Preferably, there can be a plurality of stop pillars (120) symmetrically distributed on two side edges of the second cover portion (12). More preferably, for matching with an arc surface of the lid body (23), an outward extension distance of the stop pillar(s) (120) disposed closer to a central region of the second cover portion (12) would be shorter than the stop pillar(s) (120) disposed away from the central region of the second cover portion (12). However, the present invention is not limited thereto. A person skilled in the art can change the length or distribution of the stop pillar(s) (120) for corresponding to the shape of the lid body (23) if needed. It is worth mentioned that if the second cover portion (12) is clamped with the lid body (23) through a direct "surface contact", it would fit too tightly to remove easily. Instead of said "surface contact", if the stop pillar(s) (120) is "point-contacted" with the lid body (23), detaching the physiological detection device (10) from the lid body (23) will become easier.

Preferably, the bottom portion (17) of the physiological detection device (10) further includes a power unit (18) for serving as a power source of the physiological detection device (10). Preferably, the power unit (18) is disposed in a holding notch of the physiological detection device (10), and an opening of the holding notch is sealed with a cell lid which can be opened by rotation. More preferably, the power unit (18) is a button cell battery.

Figure 5:
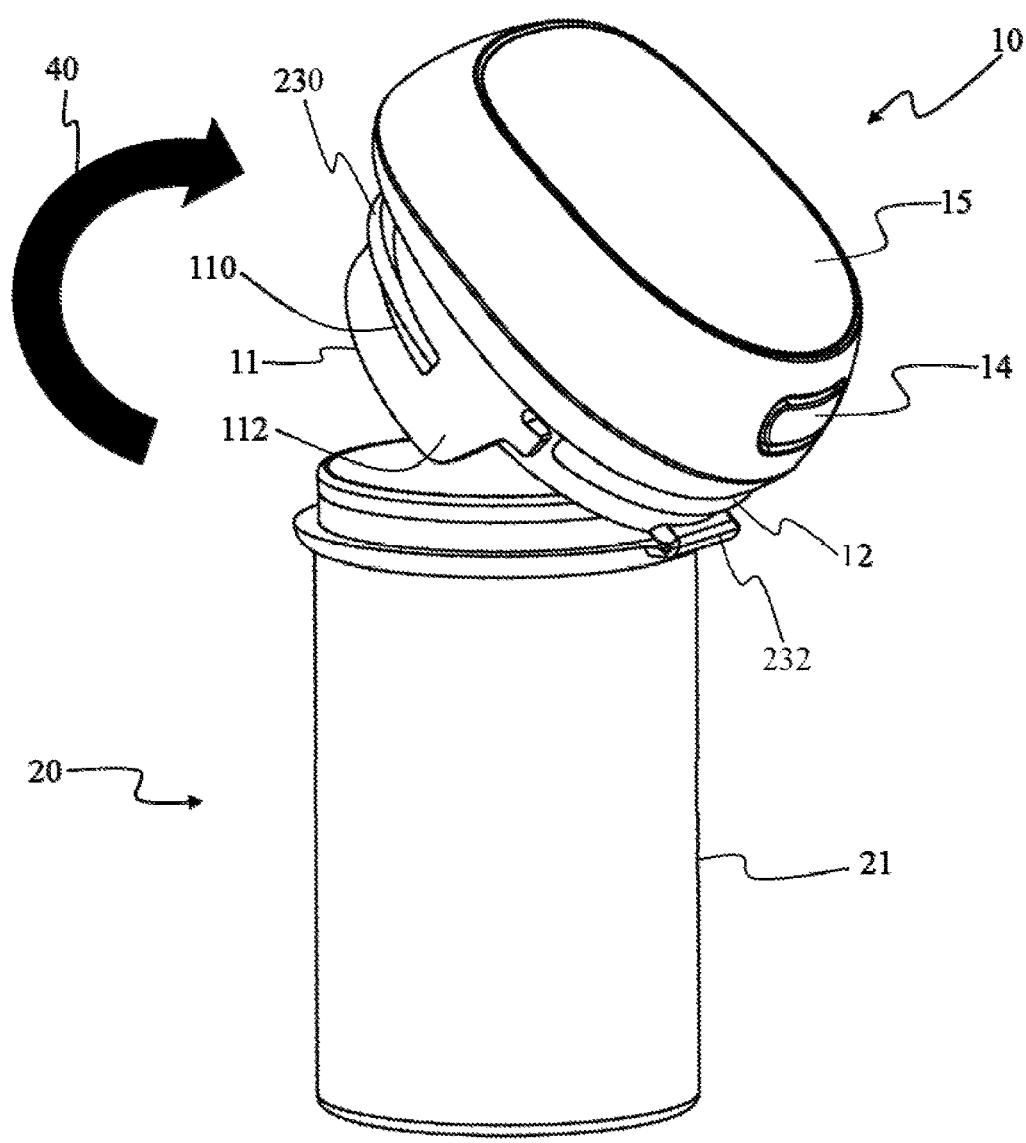
FIG. 5 shows a schematic view illustrating a physiological detection device of a second preferred embodiment according to the present invention, which is mounted on a container and a lid body is opened.

FIG. 5 shows a schematic view illustrating the physiological detection device of a second preferred embodiment according to the present invention, which is mounted to a container and a lid body is opened. FIG. 6 shows a schematic view illustrating the physiological detection device of a second preferred embodiment according to the present invention, which is mounted to a container and is in a use state. Please refer to FIG. 3 to FIG. 6, use of the container (20) together with the physiological detection device (10) will be further described below. In the embodiment, when the first cover portion (11) of the physiological detection device (10) getting close to the flange portion (230) of the lid body (23), a force is applied on the physiological detection device (10) along a direction toward the pivot portion (232), such that the physiological detection device (10) is mounted on the lid body (23). Preferably, applying the force along the direction toward the pivot portion (232) includes using the flange portion (230) as a fulcrum and generating a torque to rotate the device downward toward the lid body (23). More specifically, the flange portion (230) of the lid body (23) can be exposed from the engaging portion (110) of the first cover portion (11), and the interference portion (112) is clamped on the lid body (23) and/or the main body (21) through application of a force.

When the physiological detection device (10) is mounted on the lid body (23), a force can be applied on the first cover portion (11) along a lid opening direction (40), such that the physiological detection device (10) is fixed on the lid body (23) by stopping the force applied along the lid opening direction (40) by the second cover portion (12), and the lid body (23) is opened. More specifically, when the lid body (23) is opened, the lid body (23) and the main body (21) only connected with each other through the pivot portion (232). At this time, a user can take the disposable material (30) stored in the main body (21) out.

The user may press an operating unit (14) of the physiological detection device (10), which is coupled to a micro processing unit (not shown) for operating the physiological detection device (10). More specifically, the operating unit (14) is configured to set the physiological detection device or to query the data measured by the physiological detection device. Preferably, the operating unit (14) is a button. However, the present invention is not limited thereto. The disposable material (30) taken out from the container (20) can be inserted into an opening (13) of the physiological detection device (10). The opening (13) is configured for accommodating the disposable material (30). For example, the opening (13) can be a connector for accommodating a blood glucose test strip, and a user can drop the blood onto the blood glucose test strip. The micro processing unit of the physiological detection device (10) is configured for performing a detection of a physiological parameter. The display unit (15) is coupled to the micro processing unit to display a related information of the physiological detection device (10). The related information includes but not limited to detection results, messages related to detection procedures or operation errors, battery power level, and the set time and date. Preferably, the display unit (15) is a liquid crystal display (LCD) screen, but the present is not limited thereto. For example, when exceeding a predetermined time period and the blood amount dropped on the blood glucose test strip is not enough, the display unit (15) is configured to display an error message for reminding the user to replace another blood glucose test strip. Also, for example, the display unit (15) is configured to display the physiological parameter detected when the detection of the parameter is finished.

When a user wants to remove the physiological detection device (10) from the lid body (23), a force is applied along a direction away from the pivot portion (232), such that the physiological detection device (10) can be removed from the lid body (23). Preferably, the direction away from the pivot portion (232) is a direction through which the flange portion (230) is used as a fulcrum, and a torque to rotate the device upward relative to the lid body (23) is generated.

Although above mentioned embodiments have already described possible configurations of the lid opening structure and physiological detection device, a person skilled in the art should understand that designs of the lid opening structure and physiological detection device can be different among manufacturers. Therefore, the application of the present invention is not limited to these possible configurations. In other words, as long as the following condition is fulfilled, it should be considered within the spirit of the present invention: the physiological detection device can be mounted on or detached from a container by applying a force along a single direction, and the physiological detection device can still be fixed on the lid body by utilizing the lid opening structure when opening the container, such that the combined use of the physiological detection device and the container at the same time can be realized. For making a person skilled in the art further understands the spirit of the present invention and implements the invention, more embodiments are provided below.

In above embodiments shown in FIG. 1A to FIG. 1D, the physiological detection device (10) is provided for measuring at least one physiological parameter. However, it is only an alternative embodiment. In other embodiments, a person skilled in the art can select the amount and types of detection targets based on needs. Taking a drug test for example, the physiological detection device may detect a variety of targets, and the targets may be selected form a group consisting of cocaine (COC), tetrahydrocannabinol (THC), methamphetamine (MET), amphetamine (AMP), ecstasy (3,4-Methylenedioxymethamphetamine, MDMA), morphine (OPI), phencyclidine (PCP), benzodiazepines (BZO), barbiturates (BAR), methadone (MTD), tri-cyclic antidepressants (TCA), oxycodone (OXY) and combinations thereof. The above targets can be freely selected; however, detections of MET and AMP cannot be performed on a same test paper since they have similar structures and the detection results may be interfered.

In the embodiments shown in FIG. 2A to FIG. 2D and FIG. 5, the engaging portion (110) is configured for clamping the flange portion (230). More preferably, the engaging portion (110) is an aperture, and the flange portion (230) of the lid body (23) is exposed from the engaging portion (110) of the first cover portion (11). However, it is only an alternative embodiment. A person skilled in the art can alter the configurations of the engaging portion if needed. For example, the engaging portion can be protrusion-shaped, and the profile of the protrusion is corresponding to the shape of the flange portion.

In the embodiments shown in FIG. 2A to FIG. 2D and FIG. 3, the physiological detection device (10) further includes a guide portion (1120) for guiding the physiological detection device (10) to be prepared for being mounted on the lid body (23). Preferably, the guide portion (1120) is a notch. However, it is only an alternative embodiment. A person skilled in the art can change the position and shape of the guide portion if needed. In other embodiments, the guide portion can be disposed on the second cover portion, or separately disposed on the bottom portion of the physiological detection device. The guide portion can provide an instruction regarding the orientation for mounting the physiological detection device on the lid body for the user through different colors or shapes. For example, the guide portion can be a red triangular shape, and an edge of the flange portion can have a corresponding pattern.

In the embodiments shown in FIG. 3 and FIG. 6, the main body (21) is configured for accommodating a disposable material (30) used together with the physiological detection device (10). For example, the physiological detection device (10) is a blood glucose meter, and the disposable material (30) is a blood glucose test strip. However, it is only an alternative embodiment. A person skilled in the art can change the detection technology corresponding to the disposable material and the physiological detection device if needed. In other embodiments, the disposable material can be used for an enzymatic reaction or a chemical deposition reaction, and the physiological detection device can be an electrochemical detection device or an optical detection device.

In the embodiments shown in FIG. 5 and FIG. 6, the operating unit (14) is coupled to the micro processing unit for operating the physiological detection device (10). Preferably, the operating unit (14) is a button. However, it is only an alternative embodiment. A person skilled in the art can alter the configuration of the operating unit if needed. In other embodiments, the operating unit can be a touch-controlled unit operated by sensing touch from a user.

As above mentioned, the display unit (15) is coupled to the micro processing unit for displaying a related information of the physiological detection device (10). The related information includes but not limited to detection results, messages related to detection procedures or operation errors, battery power level, and the set time and date. Preferably, the display unit (15) is a liquid crystal display screen. However, it is only an alternative embodiment. The display unit can present above information through sounds, images, numbers, signs, lights or other forms. For example, the display unit can use a battery sign to indicate the remaining battery level. It is worth mentioned that the display unit can present the information through one or more configurations. For example, the display unit can be a red light and a voice unit. When a detection result of the physiological parameter is lower than a standard value, the voice unit can speak the detection result value of the physiological parameter and at the same time the red light is lighted up or flashing to indicate that the parameter is lower than the standard value.

To sum up, a lid opening structure and a physiological detection device provided in the present invention allow a physiological detection device to be mounted on or detached from a lid body of a container by applying a force along a single direction. The use of the physiological detection device and the container can be combined through simple operations. In particular, the direction of the force applied for mounting or detaching is quite intuitional, and complex structural designs or assembling procedures that may cause a senior to forget how to assemble are avoided. Furthermore, the preferred embodiments of the present invention may have the following effects.

1. The physiological detection device provided in the present invention can be mounted on or detached from a container by applying a force along a single direction. It is convenient that the detection related items can be stored and accessed at the same time, and a situation in which an item is lost due to separate or improper storage can be prevented.

2. The lid opening structure provided in the present invention utilizes a simple structure to fix the physiological detection device on the lid body of the container. The detection related material stored in the container can be taken out and used on the physiological detection device immediately, thus detection steps can be performed more smoothly.

3. The physiological detection device of the present invention is adapted to a universal lid body through a lid opening structure, and there is no need to arrange an additional corresponding clamp structure on the lid body, such that the time for redesigning a container and the manufacture cost for creating a new production line can be saved. The product can be put in the marketplace directly and the schedule for product launch can be shortened. The compatibility of the product and a general container product is also elevated.

Although the present invention has been disclosed based on above embodiments, it will be apparent to those skilled in the art that various modifications and variations can be made to the structure of the present invention without departing from the scope or spirit of the present invention. In view of the foregoing, it is intended that the present invention cover modifications and variations that fall within the scope of the following claims and their equivalents.

What is claimed is:

1. A lid opening structure adapted for a physiological detection device and for being mounted on a lid body of a container, wherein the lid body comprises a flange portion and a pivot portion, the flange portion is disposed in a side of the lid body opposite to the pivot portion, and the pivot portion is configured to connect a main body and the lid body of the container, the lid opening structure comprising:
   a first cover portion for covering part of outside of the lid body, and including an engaging portion for clamping the flange portion of the lid body to fixed the physiological detection device on the lid body when applying a force on the physiological detection device along a lid opening direction; and
   a second cover portion shaped as a thin wall positioned relative to the pivot portion for covering the other part of outside of the lid body.

2. The lid opening structure according to claim 1, wherein the first cover portion further comprises an interference portion disposed on ends of two side edges of the first cover portion and configured for clamping the lid body and/or the main body.

3. The lid opening structure according to claim 2, wherein each of the first cover portion and the second cover portion is a thin wall with a uniform thickness, the interference portion is a thickened portion of the thin wall, the engaging portion is an aperture, and a length of the engaging portion is corresponding to a length of the flange portion.

4. The lid opening structure according to claim 1, further comprising a guide portion for guiding the physiological detection device to be mounted on the lid body.

5. The lid opening structure according to claim 4, wherein the guide portion is a notch, which is disposed on ends of two side edges of the first cover portion to provide a space for deformation of the interference portion when the physiological detection device being mounted on or detached from the lid body.

6. The lid opening structure according to claim 1, wherein a length of the first cover portion is longer than half of a perimeter of the lid body matched with the first cover portion, and the second cover portion is disposed in a position of the lid opening structure corresponding to a peripheral portion of the lid body which does not covered by the first cover portion.

7. The lid opening structure according to claim 1, wherein the second cover portion further comprises a stop pillar, which is disposed on an inner side surface of the second cover portion, and is extended outward from the inner side surface of the second cover portion.

8. The lid opening structure according to claim 7, wherein there is a plurality of stop pillars symmetrically distributed on two parts of the inner side surface of the second cover portion.

9. The lid opening structure according to claim 1, wherein the container is configured for storing a disposable material used together with the physiological detection device.

10. A physiological detection device adapted for being mounted on a container, wherein the container comprises a lid body and a main body, the lid body comprises a flange portion and a pivot portion, the flange portion is disposed in a side of the lid body opposite to the pivot portion, and the pivot portion is configured to connect a main body and the lid body of the container, the physiological detection device comprising:
- a first cover portion for covering part of outside of the lid body, and including:
- an engaging portion for clamping the flange portion of the lid body to fixed the physiological detection device on the lid body when applying a force on the physiological detection device along a lid opening direction; and
- an interference portion disposed on two side edges of the first cover portion and is-configured for clamping the lid body and/or the main body.

11. The physiological detection device according to claim 10, further comprising a guide portion for guiding the physiological detection device to be mounted on the lid body.

12. The physiological detection device according to claim 11, wherein the guide portion is a notch, which is disposed on ends of two side edges of the first cover portion to provide a space for deformation of the interference portion when the physiological detection device being mounted on or detached from the lid body.

13. The physiological detection device according to claim 10, wherein a length of the first cover portion is longer than half of a perimeter of the lid body.

14. The physiological detection device according to claim 10, further comprising a second cover portion shaped as a thin wall positioned relative to the pivot portion.

15. The physiological detection device according to claim 14, wherein each of the first cover portion and the second cover portion is a thin wall with a uniform thickness, the interference portion is a thickened portion of the thin wall, the engaging portion is an aperture, and a length of the engaging portion is corresponding to a length of the flange portion, and the second cover portion further comprises a stop pillar, which is disposed on an inner side surface of the second cover portion, and is extended outward from the inner side surface of the second cover portion.

16. The physiological detection device according to claim 15, wherein there is a plurality of stop pillars symmetrically distributed on two parts of the inner side surface of the second cover portion.

17. The physiological detection device according to claim 10, further comprising an opening for accommodating a disposable material used together with the physiological detection device.

18. The physiological detection device according to claim 10, wherein the physiological detection device is a blood glucose meter, and the container is a test strip vial.

19. The physiological detection device according to claim 10, further comprising:
- a micro processing unit for performing a detection of a physiological parameter; and
- a display unit coupled to the micro processing unit, which is configured to display a related information of the physiological detection device.

20. The physiological detection device according to claim 19, further comprising:
- a power unit disposed on a bottom portion of the physiological detection device for serving as a power source of the physiological detection device; and
- an operating unit coupled to the micro processing unit for operating the physiological detection device.

* * * * *